US00PP34160P2

(12) United States Plant Patent
Barnes

(10) Patent No.: US PP34,160 P2
(45) Date of Patent: Apr. 19, 2022

(54) ***SALVIA* PLANT NAMED 'WNSVUPPK'**

(50) Latin Name: *Salvia hybrida*
Varietal Denomination: WNSVUPPK

(71) Applicant: Brent D. Barnes, Riverside, CA (US)

(72) Inventor: Brent D. Barnes, Riverside, CA (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 17/371,530

(22) Filed: Jul. 9, 2021

(51) Int. Cl.
*A01H 6/50* (2018.01)
*A01H 5/02* (2018.01)

(52) U.S. Cl.
USPC ..... Plt./475

(58) Field of Classification Search
USPC ..... Plt./475
See application file for complete search history.

*Primary Examiner* — Annette H Para
(74) *Attorney, Agent, or Firm* — C. Anne Whealy

(57) ABSTRACT

A new and distinct cultivar of *Salvia* plant named 'WNSVUPPK', characterized by its upright to somewhat outwardly spreading plant habit; vigorous growth habit and rapid growth rate; freely branching habit; dense and bushy plant form; strong and sturdy lateral branches; very dark green-colored leaves; early and freely flowering habit; upright inflorescences with purplish red-colored flowers; and good garden performance.

2 Drawing Sheets

Figure 1:
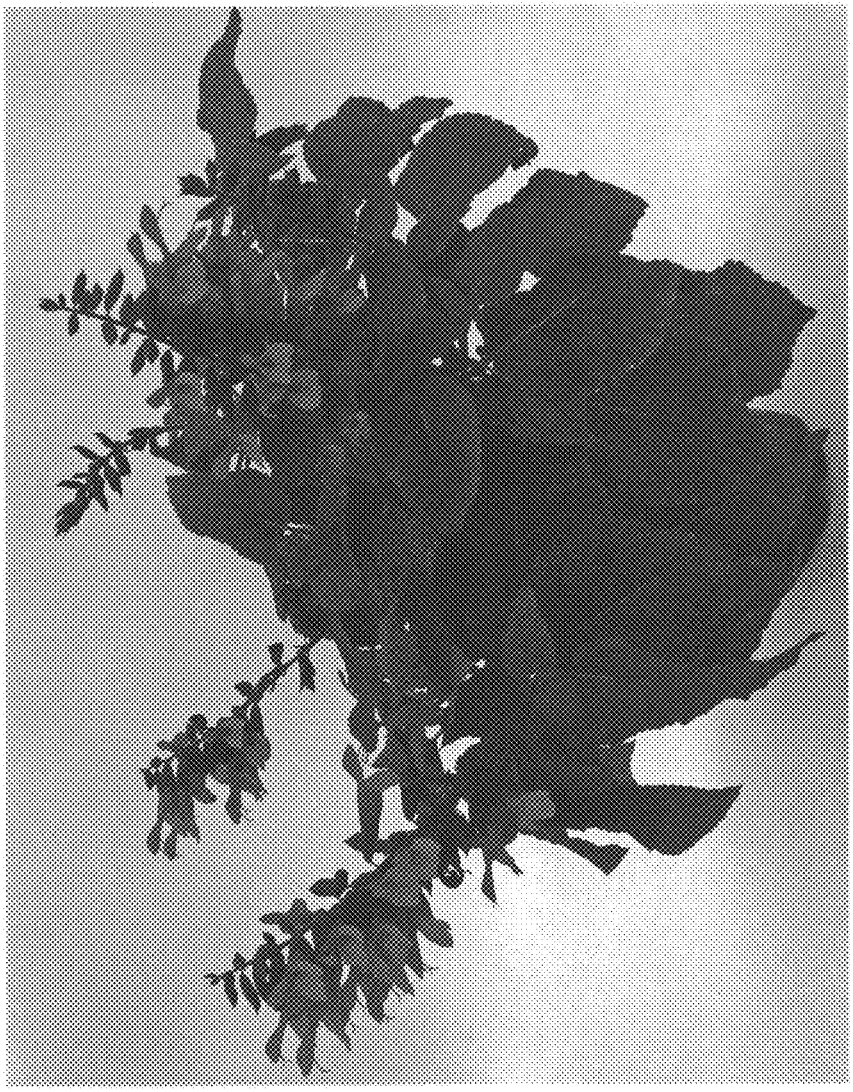

Botanical designation: *Salvia hybrida.*
Cultiovar denomination: 'WNSVUPPK'.

BACKGROUND OF THE INVENTION

The present invention relates to a new and distinct cultivar of *Salvia* plant, botanically known as *Salvia hybrida* and hereinafter referred to by the name 'WNSVUPPK'.

The new *Salvia* plant is a product of a planned breeding program conducted by the Inventor in Bonsall, Calif. The objective of the breeding program is to create new compact and uniform *Salvia* plants with attractive leaves and flowers and good garden performance.

The new *Salvia* plant originated from a cross-pollination made by the Inventor on Aug. 24, 2016 of a proprietary selection of *Salvia hybrida* identified as code number 16SB131-01, not patented, as the female, or seed, parent with *Salvia hybrida* 'BBSAL00301', disclosed in U.S. Plant Pat. No. 30,923, as the male, or pollen, parent. The new *Salvia* plant was discovered and selected by the Inventor as a single flowering plant from within the progeny of the stated cross-pollination in a controlled greenhouse environment in Bonsall, Calif. on Aug. 16, 2017.

Asexual reproduction of the new *Salvia* plant by vegetative terminal cuttings in Bonsall, Calif., since Aug.23, 2017 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNSVUPPK'. These characteristics in combination distinguish 'WNSVUPPK' as a new and distinct *Salvia* plant:

1. Upright to somewhat outwardly spreading plant habit.
2. Vigorous growth habit and rapid growth rate.
3. Freely branching habit; dense and bushy plant form.
4. Strong and sturdy lateral branches.
5. Very dark green-colored leaves.
6. Early and freely flowering habit.
7. Upright inflorescences with purplish red-colored flowers.
8. Good garden performance.

Plants of the new *Salvia* can be compared to plants of the female parent selection. Plants of the new *Salvia* differ primarily from plants of the female parent selection in the following characteristics:

1. Plants of the new *Salvia* are shorter than plants of the female parent selection.
2. Plants of the new *Salvia* are more freely branching and denser than plants of the female parent selection.
3. Plants of the new *Salvia* have stronger and sturdier lateral branches than plants of the female parent selection.
4. Plants of the new *Salvia* are more tolerant to full sunlight conditions than plants of the female parent selection.

Plants of the new *Salvia* can be compared to plants of the male parent, 'BBSAL00301'. Plants of the new *Salvia* differ primarily from plants of 'BBSAL00301' in the following characteristics:

1. Plants of the new *Salvia* are shorter than plants of 'BBSAL00301'.
2. Plants of the new *Salvia* are more tolerant to full sunlight conditions than plants of 'BBSAL00301'.

Plants of the new *Salvia* can be compared to plants of *Salvia hybrida* 'Amistad', disclosed in U.S. Plant Pat. No.

23,578. In side-by-side comparisons, plants of the new *Salvia* differ from plants of 'Amistad' in the following characteristics:

1. Plants of the new *Salvia* are shorter and more upright than plants of 'Amistad'.
2. Plants of the new *Salvia* are more freely branching and denser than plants of 'Amistad'.
3. Plants of the new *Salvia* have stronger and sturdier lateral branches than plants of 'Amistad'.
4. Leaves of plants of the new *Salvia* are broader and darker green in color than leave of plants of 'Amistad'.

Plants of the new *Salvia* can also be compared to plants of *Salvia guaranitica* 'Black and Blue', not patented. In side-by-side comparisons, plants of the new *Salvia* differ from plants of 'Black and Blue' in the following characteristics:

1. Plants of the new *Salvia* are more compact than plants of 'Black and Blue'.
2. Plants of the new *Salvia* are more freely branching and denser than plants of 'Black and Blue'.
3. Plants of the new *Salvia* have stronger and sturdier lateral branches than plants of 'Black and Blue'.
4. Leaves of plants of the new *Salvia* are broader and darker green in color than leaves of plants of 'Black and Blue'.
5. Plants of the new *Salvia* flower earlier than plants of 'Black and Blue'.
6. Flowers of plants of the new *Salvia* are purplish red in color whereas flowers of plants of 'Black and Blue' are blue in color.

BRIEF DESCRIPTION OF THE PHOTOGRAPHS

The accompanying colored photographs illustrate the overall appearance of the new *Salvia* plant showing the colors as true as it is reasonably possible to obtain in colored reproductions of this type. Colors in the photographs may differ slightly from the color values cited in the detailed botanical description which accurately describe the colors of the new *Salvia* plant.

The photograph on the first sheet (FIG. 1) is a side perspective view of a typical flowering plant of 'WNSVUPPK' grown in a container.

Figure 2:
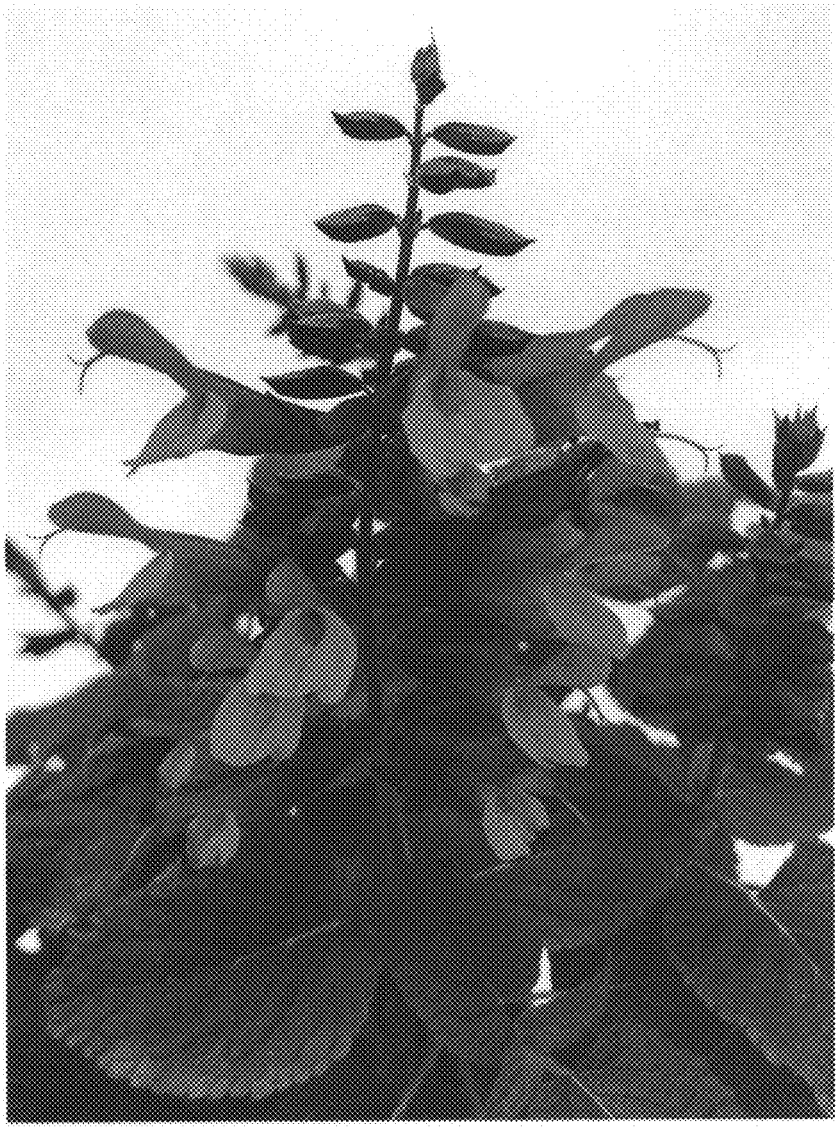

The photograph on the second sheet (FIG. 2) is a close-up view of a typical flowering plant of 'WNSVUPPK'.

DETAILED BOTANICAL DESCRIPTION

The aforementioned photographs and following observations and measurements describe plants grown during the autumn and winter in 10.8-cm containers in a glass-covered greenhouse in Loudon, N.H. and under cultural practices typical of commercial *Salvia* production. During the production of the plants, average daily temperatures were 18° C. Plants were grown under long day/short night conditions and were pinched two weeks after planting. Plants were ten weeks from planting when the photographs and description were taken. In the following description, color references are made to The Royal Horticultural Society Colour Chart, 2015 Edition, except were general terms of ordinary dictionary significance are used. Measurements were taken on individual plants.

Botanical classification: *Salvia hybrida* 'WNSVUPPK'.

Parentage:

*Female, or seed, parent.*—Proprietary selection of *Salvia hybrida* identified as code number 16SB131-01, not patented.

*Male, or pollen, parent.*—*Salvia hybrida* 'BBSAL00301', disclosed in U.S. Plant Pat. No. 30,923.

Propagation:

*Type.*—By vegetative terminal cuttings.

*Time to initiate roots, summer.*—About three days at ambient temperatures about 17° C. to 29° C.

*Time to initiate roots, winter.*—About five days at ambient temperatures about 17° C. to 21° C.

*Time to produce a rooted young plant from unrooted cuttings, summer.*—About 14 days at ambient temperatures about 17° C. to 29° C.

*Time to produce a rooted young plant from unrooted cuttings, winter.*—About 17 days at ambient temperatures about 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial typically grown as a container and garden plant; upright to somewhat outwardly spreading plant habit; uniform plant and flowering habit; vigorous growth habit and rapid growth rate.

*Branching habit.*—Freely basal branching with lateral branches potentially developing at every node; bushy and dense appearance.

*Plant height, soil level to top of foliar plane.*—About 20 cm.

*Plant height, soil level to top of floral plane.*—About 28 cm.

*Plant width.*—About 41 cm.

*Lateral branch description.*—Length: About 18 cm. Diameter: About 5 mm to 6 mm. Internode length: About 3 cm. Strength: Strong and sturdy. Aspect: Mostly upright to about 30° to 45° from vertical; curving upright. Texture and luster: Densely pubescent, longitudinally ridged; matte. Color, developing and developed: Close to 146A variably tinged with close to 187A.

Leaf description:

*Arrangement.*—Opposite, simple.

*Length.*—About 9 cm.

*Width.*—About 8 cm.

*Shape.*—Ovate.

*Apex.*—Acuminate.

*Base.*—Cordate.

*Margin.*—Crenate to serrate with shallow indentations.

*Texture and luster, upper surface.*—Smooth, glabrous; moderately glossy.

*Texture and luster, lower surface.*—Smooth, glabrous; slightly glossy.

*Venation pattern.*—Pinnate, reticulate.

*Fragrance.*—Pungent; not unpleasant.

*Color.*—Developing leaves, upper surface: More green than N189A. Developing leaves, lower surface: Close to 147A. Fully expanded leaves, upper surface: More green than N189A; venation, close to 146A. Fully expanded leaves, lower surface: Close to 147A; venation, close to 146B to 146C.

*Petioles.*—Length: About 5.1 cm. Diameter: About 4 mm. Strength: Moderately strong; flexible. Texture and luster, upper and lower surfaces: Smooth, glabrous; moderately glossy. Color, upper surface: Close to 146A. Color, lower surface: Close to 146B to 146C.

Flower description:

*Flower arrangement and shape.*—Single bilabiate flowers arranged on terminal racemes; freely flowering habit with about 25 to 30 flowers developing per inflorescence; flowers face mostly outwardly.

*Fragrance.*—None detected.

*Natural flowering season.*—Early flowering habit, plants begin flowering about six to seven weeks after planting; plants flower from late spring until frost in New Hampshire.

*Flower longevity.*—Flowers last about four to five days on the plant; flowers not persistent.

*Flower buds.*—Length: About 1.5 cm. Diameter: About 5 mm. Shape: Obovate to clavate. Texture and luster: Slightly pubescence; slightly glossy. Color: Close to 187A.

*Inflorescence height.*—About 10.5 cm.

*Inflorescence diameter.*—About 8.5 cm.

*Flower height.*—About 2 cm.

*Flower diameter.*—About 1 cm.

*Flower length (depth).*—About 4.75 cm.

*Flower throat diameter.*—About 4.5 mm.

*Flower tube length.*—About 2.5 cm.

*Flower tube diameter, distally.*—About 7.5 mm by 4 mm.

*Flower tube diameter, proximally.*—About 5 mm by 3 mm.

*Petals.*—Arrangement: Five petals with two upper petals fused forming a galea and three lower petals fused forming a broader lower protruding lip. Upper galea length: About 1.75 cm. Upper galea width: About 6 mm. Lower lip length: About 1.1 cm. Lower lip width: About 1.1 cm. Shape: Upper galea, hooded; lower lip, spatulate, revolute and incurved. Upper galea apex: Bluntly acute. Lower lip apex: Tri-lobed. Base: Fused. Margin: Entire; not undulate. Texture and luster, upper surface: Smooth, glabrous; slightly glossy. Texture and luster, lower surface: Smooth, glabrous; slightly to moderately glossy. Texture and luster, throat: Smooth, glabrous; slightly glossy. Texture and luster, tube: Sparsely pubescent; slightly to moderately glossy. Color: Galea, when opening and fully opened, upper surface: Close to 72A; venation, close to 72A; color does not change with subsequent development. Galea, when opening and fully opened, lower surface: Close to 72A; venation, close to 72A; color does not change with subsequent development. Lower lip, when opening and fully opened, upper surface: Close to 72A; venation, close to 72A; color does not change with subsequent development. Lower lip, when opening and fully opened, lower surface: Close to 72A; venation, close to 72A; color does not change with subsequent development. Throat: Close to between 72A and 77A; venation, close to between 72A and 77A. Tube: Close to between 72A and 77A; venation, close to between 72A and 77A.

*Calyx.*—Arrangement: Three sepals fused to form a tubular bilabiate calyx. Calyx length: About 1.6 cm. Calyx diameter: About 7 mm by 4 mm. Sepal length: About 1.6 cm. Sepal width: About 5 mm. Sepal shape: Lanceolate. Sepal apex: Acuminate. Sepal margin: Entire. Sepal texture and luster, inner surface: Smooth, glabrous; moderately glossy. Texture and luster, outer surface: Slightly pubescent; slightly glossy. Color: When developing and fully developed, inner surface: Close to 187A; proximally, close to 148A to 148B. When developing and fully developed, outer surface: Close to 187A.

*Peduncles.*—Length: About 8 cm. Diameter: About 2.5 mm. Strength: Strong. Aspect: Mostly erect. Texture and luster: Smooth, glabrous; matte; longitudinally ridged. Color: Close to 187A.

*Pedicels.*—Length: About 3 mm. Diameter: Less than 1 mm. Strength: Strong, flexible; wiry. Aspect: About 45° from peduncle axis. Texture and luster: Moderately to densely pubescent; matte. Color: Close to N187A.

*Reproductive organs.*—Stamens: Quantity per flower: Two. Filament length: About 1.75 cm. Filament color: Distally, close to NN155D and proximally, close to 72A. Anther size: About 5 mm by 1.5 mm. Anther shape: Oblong. Anther color: Close to 187A. Pollen amount: Moderate. Pollen color: Close to 10C. Pistils: Quantity per flower: One. Pistil length: About 3.4 cm. Stigma diameter: Less than 1 mm. Stigma shape: Bipartite. Stigma color: Close to 71A. Style length: About 2.9 cm. Style color: Distally, close to 71A and proximally, close to NN155D. Ovary color: Close to 154D.

*Seeds and fruits.*—To date, seed and fruit production has not been observed on plants of the new *Salvia* plant.

Pathogen & pest resistance: To date, plants of the new *Salvia* have not been noted to be resistant to pathogens and pests common to *Salvia* plants.

Garden performance: Plants of the new *Salvia* have exhibited good garden performance and to be tolerant to rain, wind, low temperatures about 2° C. and to be suitable for USDA Hardiness Zone 10a to 11b.

It is claimed:

1. A new and distinct *Salvia* plant named 'WNSVUPPK' as illustrated and described.

* * * * *